United States Patent [19]

Gasser et al.

[11] Patent Number: 4,882,365

[45] Date of Patent: Nov. 21, 1989

[54] POLYMERIZABLE RADIOPAQUE DENTAL COMPOSITION

[75] Inventors: Oswald Gasser, Seefeld; Klaus Ellrich, Wörthsee, both of Fed. Rep. of Germany

[73] Assignee: ESPE Stiftung & Co. Produktions- und Vertriebs KG, Seefeld, Fed. Rep. of Germany

[21] Appl. No.: 231,190

[22] Filed: Aug. 11, 1988

Related U.S. Application Data

[62] Division of Ser. No. 27,326, Mar. 18, 1987, Pat. No. 4,767,798.

[30] Foreign Application Priority Data

Mar. 18, 1986 [DE] Fed. Rep. of Germany ....... 3609038

[51] Int. Cl.$^4$ .......................... C08K 3/10; A61K 6/08
[52] U.S. Cl. ..................................... 523/117; 524/783
[58] Field of Search .......................... 523/117; 524/783

[56] References Cited

U.S. PATENT DOCUMENTS

| | | | |
|---|---|---|---|
| 3,971,754 | 7/1976 | Jurecic | 523/117 |
| 4,040,846 | 8/1977 | Broemer et al. | 501/42 |
| 4,136,073 | 1/1979 | Muro et al. | 524/783 |
| 4,372,836 | 2/1983 | Schmitt et al. | 524/783 |
| 4,629,746 | 12/1986 | Michl et al. | 523/117 |

OTHER PUBLICATIONS

Derwent Abs 80-30039C/17 Toyo Seikaku Kasei J55035015 (3-1980).

*Primary Examiner*—Herbert J. Lilling
*Attorney, Agent, or Firm*—Becker & Becker, Inc.

[57] ABSTRACT

A polymerizable, radiopaque dental composition including: one or more ethylenically unsaturated, polymerizable monomer and/or polymer, possible conventional fillers, pigments, initiators, activators, and thixotropic auxiliary material, as well as, in addition, a heavy-metal fluoride with very low solubility selected from the group consisting of complex heavy-metal fluorides having the general formula $M^{II}M^{IV}F_6$, where $M^{II}$ is a calcium, strontium, or barium ion, and $M^{IV}$ is a titanium, zirconium, or hafnium ion. These filler compositions exhibit excellent X-ray visibility along with excellent optical properties.

8 Claims, No Drawings

POLYMERIZABLE RADIOPAQUE DENTAL COMPOSITION

This is a divisional application of copending parent application Ser. No. 027,326—Gasser et al filed Mar. 18, 1987, now U.S. Pat. No. 4,767,798—Gasser et al. dated Aug. 30, 1988 and belonging to the assignee of the present invention.

BACKGROUND OF THE INVENTION

1. Field of the Invention

The present invention relates to a novel polymerizable, radiopaque dental composition, especially for fillings for teeth.

2. Description of the Prior Art

A majority of the commercial tooth-filling compositions have only a slightly X-ray absorption. As a result, it is not possible for the treating dentist to see, for example, an existing tooth filling, or to be able to differentiate the filling from the surrounding tooth material, on an X-ray photograph made with equipment used in the dentist's office. An examination of the existing filling is thus only superficially possible, especially after the filling has been in place for a longer period of time. The formation of marginal gaps or cracks along the edges, changes in the surrounding tooth material (especially below the filling), as well as loss of material cannot be controlled by the dentist with non-radiopaque dental compositions; thus, such compositions could lead to further damage to the teeth of the patient.

Furthermore, excess filling material, which can resulting in difficult-to-see locations (for example in the approximal region), is often difficult to discover if it doesn't show up on an X-ray photograph.

This result especially in recent times, has increasingly led to the sale of a series of polymerizable, radiopaque dental compositions. Commercial preparations generally contain barium, strontium, lanthanum, or zinc-containing glass or silica, such as known, for example, from German Offenlegungsschrift No. 23 47 591 Müller of Apr. 3, 1975, and U.S. Pat. No. 3,808,170-Rogers dated Apr. 30, 1974 Dietz dated Aug. 17, 1976 or radiopaque additives together with other commercial fillers, such as quartz, certain lithium aluminum silicates, silicic acids, silica gel, or silicic acid granules. Examples of radiopaque additives include barium sulfate, zirconium oxide, or lanthanum oxide. U.S. patents 3,971,754-Jurecic dated June 27, 1976 and 3,801,344 Dietz dated Apr. 2, 1974 disclose ceramic filler compounds which, among other things, contain oxides of lanthanum, hafnium, and the lanthanide series metals. For an optimum application, radiopaque dental compositions should have a greater X-ray visibility than does human dentine. Normally, the X-ray visibility of materials is expressed in mm aluminum per mm material. For example, human dentine has an X-ray visibility of approximatey 1.5 mm aluminum. In other words, radiopaque dental compositions should have an X-ray visibility of greater than 1.5 mm aluminum.

However, with the aforementioned, heretofore known additives, and the ceramic filler compositions, such an X-ray visibility is achieved only if at the same time a loss in the transparency of the polymerized material is accepted. Unfortunately, this means that the cosmetic appearance of this material can no longer be optimally adapted to the surrounding tooth material. The transparency of the polymerized material depends largely on the ratio of the index of refraction of the filling material to the polymer matrix. Although the indexes of refraction of monomers and polymers do not differ much, being in the range of 1.45 to 1.6 for commercially available polymerizable dental compositions, radiopaque additives do in fact exhibit great differences; in particular, the heretofore known radiopaque additives have an index of refraction of greater than 1.6. However, dental compositions having too great an opacity not only have a cosmetic drawback but, where preparations are involved that should be hardened with light, additionally lead to an insufficient depth of polymerization, since the light required for the curing can no longer penetrate deep enough into the composition. This often leads to faulty applications, with non-polymerized material existing below the cured surface; the consequence of this non-polymerized material can then be further damage to the tooth. In addition, the quality of the cured or hardened composition is unsatisfactory due to the non-cured material disposed below it.

For this reason, most commercial radiopaque dental compositions contain no radiopaque additives. Rather, all or at least a very great proportion of the filler content comprises radiopaque glass or silica, with which a sufficient transparency and satifactory X-ray visibility can be achieved. Unfortunately, tooth-filling compositions having such glass fillers can no longer achieve the physical properties that can be achieved with other fillers. These last-mentioned compositions are generally hydrolytically susceptible, which means they can be washed out at the surface over a period of time. Their color stability is sometimes not satisfactory, and above all their physical properties deteriorate far quicker than do those of compositions filled with other fillers, such as quartz. Thus, due to the lesser hardness of glass relative to quartz, toothfilling compositions produced with glass are less resistant to abrasion. Furthermore, it is not possible to grind the glass as fine, so that toothfilling compositions that can be highly polished cannot be produced with such glass fillers. Up to now this was only possible with so-called microfiller preparations, or with tooth-filling compositions that contain granules of such very small primary particles. A dental composition that is capable of being highly polished should contain only such filling material that has primary particles sizes of less than 1 um. Glass ground this fine becomes opaque due to the grinding process that is necessary to accomplish this, so that again the same drawbacks result as with other radiopaque additives.

An object of the present invention therefore is to provide novel, polymerizable, radiopaque tooth-filling compositions that do not have the drawbacks of the known compositions and with which, especially simultaneously, an excellent X-ray visibility and excellent optical properties are realized.

This object, and other objects and advantages of the present invention, will appear more clearly from the following specification in conjunction with the accompanying Examples.

SUMMARY OF THE INVENTION

To realize this object, the polymerizable, radiopaque dental composition of the present invention comprises: one or more ethylenically unsaturated polymerizable monomer and/or polymer, as well as, if desired, appropriate conventional fillers, pigments, initiators, activators, and thixotropic auxiliary material, and in addition heavy-high metal fluoride with very low solubility selected from the group consisting of VF$_3$ and complex heavy-metal fluorides having the general formula M$^{II}$-M$^{IV}$F$_6$, where M$^{II}$ is a calcium, strontium, or barium ion, and M$^{IV}$ is a titanium, zirconium, or hafnium ion.

Pursuant further to the present invention, the novel polymerizable, radiopaque dental composition can contain:

(a) up to 50% by weight ethylenically unsaturated polymerizable monomer and/or polymer, (b) 30–70% by weight conventional fillers, pigments, and possibly thixotropic auxiliary material, (c) 0.01–5% by weight polymerization initiators and possibly activators, and (d) 5–30% by weight heavy-metal fluoride with very low solubility selected from the group consisting of YF$_3$ and complex heavy-metal fluorides having the general formula M$^{II}$M$^{IV}$F$_6$, with all of the percentages relating to the total composition.

The inventive radiopaque additives of heavymetal fluorides can be 5–30% by weight, preferably 10–30% by weight and especially 10–20% by weight of the total tooth-filling composition. A proportion of heavy-metal fluoride that has been shown to be suitable in practice is approximately 15% by weight of the total composition.

The heavy-metal fluorides with very low solubility preferably have an index of refraction in the range of from 1.45 to 1.60.

The inventive polymerizable, radiopaque toothfilling compositions have the great advantage that they combine excellent X-ray visibility with excellent optical and cosmetic properties. On the one hand, the tooth-filling composition should approximate the natural appearance of a tooth in transparency and color, and on the other hand the distinction in the X-ray photograph between the tooth filling and the dental enamel enables a dentist or dental technician to judge the quality of the existing filling.

A further very significant advantage with the inventive use of heavy-metal fluorides is that even at relatively low concentrations, these fluorides result in a sufficient X-ray visibility of the dental compositions, which means that in order to achieve the necessary X-ray absorption, a relatively smaller concentration of these fluorides relative to the other fillers is necessary. Thus by adding such relatively low quantities of heavy-metal fluorides, dental compositions are obtained where the physical properties are determined by the main portion of the filler, while at the same time the composition is radiopaque. Thus, for example, the advantages of macro-fillers, namely a large proportion of filler material, resulting in less contraction, smaller thermal coefficient of expansion, and good resistance to abrasion, can be exploited, and yet the tooth-filling composition can be made radiopaque by adding the inventive fluoride.

A further advantage of using the inventive fluorides results from the simultaneous use of so-called micro-fillers. Since the fluorides can be obtained in nearly any desired granular size by precipitation reactions, it is hereby possible, together with the micro-fillers, to produce pastes that are radiopaque but nevertheless can be highly polished. Furthermore, due to the insolubility of their constituents, the inventive compositions are toxicologically harmless. The inventively utilized heavy-metal fluorides have such small solubility products that even if they are swallowed by a patient, they are not dissolved in the stomach or intestines, and can thus not be fed to the body.

For a better inclusion in the polymer matrix, it can be advantageous to make not only the conventional fillers, but also the radiopaque additive (heavy-metal fluoride) water-repellent. Customary water-repellent agents are silanes, such as methacryloxypropyltrimethoxysilane.

Ethylenically unsaturated monomers and polymers that are suitable for dental purposes include, for example, monomeric and polymeric acrylates and methacrylates. For polymerizable dental compositions, the long-chained monomers of U.S. Pat. No. 3,066,112 -Bowen dated Nov. 27, 1962 having a base of bisphenol A and glycidyl methacrylate, or derivatives thereof that result from the addition of isocyanates, are often used. Particularly suitable are the acrylates and methacrylates of monohydric or multihydric alcohols, such as methyl and ethyl methacrylate, triethylene glycol dimethacrylate, and the like. Also particularly suitable are the diacrylates and dimethacrylates of bishydroxymethyltricyclo [5.2.1.0$^{2,6}$]decane mentioned in German patent 28 16 823-Schmitt et al of Apr. 29, 1982. It is also possible to use the reaction products of diisocyanates and hydroxyalkyl(meth)acrylates, as disclosed, for example, in German Offenlegungsschrift No. 23 12 559-Foster et al of Sept. 27, 1973.

It is, of course, also possible to use mixtures of suitable monomers or unsaturated polymers derived therefrom.

In addition to saturated or unsaturated polymers, customary constituents of tooth-filling compositions familiar to one skilled in the art include pigments, dyes, and inorganic fillers. Examples of inorganic fillers are quartz, ground glass, silica gel, and silicic acids or granules thereof. These fillers can be present in a concentration of from 0–90% by weight relative to the polymerizable composition.

Suitable initiator systems include, by way of example, the redox systems suitable for cold-setting, such as peroxide/amine or peroxide/barbituric acid derivatives. When using such initiator systems, it is expedient to differentiate between an initiator (such as a peroxide) and a catalyst (such as an amine) component. The radiopaque filler can be obtained either in one component or in both components.

However, it is also possible to use, as polymerization initiators, substances that trigger polymerization after being exposed to UV or visible light, such as benzoinalkylether, benzilmonoketals, acylphosphinoxides, or aliphatic and aromatic 1,2diketo compounds, such as camphor quinone. The light polymerization can be accelerated in a known manner by the addition of activators, such as amines or organic phosphites.

The present invention will now be explained in greater in detail with the aid of several examples.

EXAMPLE 1

Production of strontium hexafluorozirconate 283.5 g (1 mole) potassium hexafluorozirconate are dissolved in 10 l warm water, and the warm solution, which is approximately at 40° C., is allowed to run through an exchanger column having 2 l cation exchanger in the H form (such as Relite CF). 147 g (1 mole) strontium carbonate is added to the filtrate, and the mixture is stirred for 16 hours at room temperature. On the next day, the mixture is aspirated, the sediment is boiled with about 5 l water for 6 hours with reflux, and the mixture is then hot-aspirated. The same procedure is repeated a second time. The again hot-aspirated sediment is dried first at 120° C., and then at 200° C..

The yield is 181.5 g, or 62% of the theoretical.

Elementary analysis shows strontium at 30.05% (calculated 29.92), and zirconium at 30.90% (calculated 31.15).

If necessary, after the boiling and aspiration, the aforementioned sediment can also be washed with acetone and then dried.

EXAMPLE 2

Production of barium hexafluorozirconate 141.8 g (0.5 mole) potassium hexafluorozirconate is dissolved in 1 l hot water; this hot mixture is added drop wise, accompanied by thorough stirring, to 122 g (0.5 mole) barium chloride dihydrate dissolved in 500 ml water. The mixture is stirred for another 30 minutes at 100° C., is aspirated, and is washed with 1 l hot water. To remove residual potassium, the material is boiled a total of five times, each time for 24 hours with reflux, and each time with 4 l water. After the final aspiration, the material is dried, the last time for two hours in a vacuum at 200° C..

The yield is 85 g, or 50% of the theoretical.

Elementary analysis shows 40.35% (calculated 40.09) barium, and 26.40% (calculated 26.63) zirconium.

EXAMPLE 3

Production of a photo polymerizable, radiopaque tooth-filling composition

A preliminary mixture is masticated from 70 parts by weight bis-acryloxymethyltricyclo [$5.2.1.0^{2,6}$]decane and 30 parts by weight 2,2-bis4-(3-methacryloxy-2-hydroxypropoxy)-phenylpropane (bis-GMA), as well as 7 parts by weight silanated pyrogenic silica, 0.3 parts by weight camphor quinone, 3 parts by weight N,N-dimethylaminoethylmethacrylate, and 110 parts by weight radiopaque filler.

5.96 g of this preliminary mixture were kneaded with a total of 12 g (paste 1) or 16 g (paste 2) or 14.8 g (paste 4) silanated and toothlike-pigmentated quartz (having an average grain size of about 6 um) to form a tooth-filling composition having a uniform pasty consistency.

As a comparison or reference paste, the same formulation (paste 3, 16 g quartz), but without any radiopaque filler, is kneaded. The results and measured physical values of the pastes obtained are presented in table 1. As a radiopaque filler, paste 1 contains barium hexafluorozirconate, paste 2 contains strontium hexafluorozirconate, and paste 4 contains yttrium fluoride. Paste 3, the referenced paste, contains no radiopaque filler.

TABLE 1

| Measured value | Paste 1 | Paste 2 | Paste 3 (reference) | Paste 4 |
|---|---|---|---|---|
| layer thickness | 8.5 mm | 8.3 mm | 8.5 mm | 8.3 mm |
| compressive strength | 316 MPa | 326 MPa | 320 MPa | 348 MPa |
| flexural strength | 102 MPa | 94 MPa | 92 MPa | 85 MPa |
| X-ray visibility | 3.0 mm Al | 2.3 mm Al | 0.5 mm Al | 1.8 mm Al |
| opacity | 87.8% | 87% | 86% | 87% |

The layer thicknesses were measured in cylindrical bodies (diameter 5 mm, length 8 mm) after irradiation with a conventional dental radiation device (Elipar/-Visio/Espe) for 20 seconds. The polymer is removed from the cylinder, the soft or gel-like, not completely polymerized components are removed with a plastic spatula, and the resulting layer thickness is measured. The X-ray visibilities are determined by producing a 1 mm test body of polymerized material and, with an aluminum step, the aluminum value is determined that corresponds to 1 mm of test material. The opacities were measured with a CIELAB colormeasuring device using test bodies having a 3.5 mm length and a 2 cm diameter. It was proven that the inventive radiopaque compositions lead to polymers that have physical properties which are equal to those of non-radiopaque material, and yet have an X-ray visibility that is sufficient for dental purposes (the X-ray visibility of human dental enamel is 1.5–2.00 mm aluminum).

EXAMPLE 4

Production of a polymerizable, radiopaque, highly polishable tooth-filling composition 45 parts by weight bis (methacryloxy)methyltricyclo [$5.2.1.0^{2,6}$]decane, 45 parts by weight bis-(acryloxymethyl)tricyclo [$5.2.1.0^{2,6}$]decane, and 10 parts by weight 2,2-bis-4-(3-methacryloxy-2-hydroxypropoxy)phenylpropane bis-4-(3-methacryloxy2-hydroxypropoxy)-phenylpropane (bis-GMA) were stirred, while being carefully heated, until a clear solution resulted.

This solution was cooled to room temperature, 0.15% by weight camphor quinone and 1.5% by weight N,N-dimethylaminoethyl methacrylate were added thereto, and this mixture was stirred until a clear initiator solution resulted.

A preliminary mixture was masticated from 50 parts by weight of this initiator solution, 32 parts by weight yttrium fluoride, 27 parts by weight silanated, pyrogenic silica.

35 parts by weight of this preliminary mixture were kneaded with 15 parts by weight silanated silica granulate (European patent No.0 040 232 Schmitt et al of Nov. 2, 1983) to form a tooth-filling composition having a uniform, pasty consistency.

The radiopaque tooth-filling composition obtained was packed into a cylinder (diameter 5 mm, length 8 mm), and was exposed for 20 seconds to radiation from a conventional dental radiation apparatus (Elipar/Visio/Espe). The polymer was subsequently removed from the cylinder, and the soft and gel-like, not completely polymerized constituents were removed with a plastic spatula. In this way, a completely polymerized layer of 6 mm was obtained. The X-ray visibility thereof was greater than 2 mm aluminum, the opacity was 92%, and the compressive strength was 385 MPa.

In summary, the present invention concerns a polymerizable, radiopaque dental composition, including the following:

at least one ethylenically unsaturated, polymerizable substance selected from the group consisting of monomers and polymers;

a heavy-metal fluoride with very low solubility selected from the group consisting of $VF_3$ and complex heavy-metal fluorides having the general formula $M^{II}M^{IV}F_6$, where $M^{II}$ is selected from the group consisting of calcium, strontium, and barium ions, and $M^{IV}$ is selected from the group consisting of titanium, zirconium, and hafnium ions; at least one of the group consisting of conventional fillers, pigments, and thixotropic auxiliary material, and also including at least one polymerization initiator; the heavy-metal fluoride is $YF_3$; and the heavy-metal fluoride has an index of refraction in the range of from 1.45 to 1.60.

The present invention is, of course, in no way restricted to the specific disclosure of the specification and examples, but also encompasses any modifications within the scope of the appended claims.

What we claim is:

1. A polymerizable, radiopaque dental composition comprising:
   at least one ethylenically unsaturated, polymerizable substance up to 50% by weight selected from the group consisting of monomers and polymers; and
   a heavy-metal fluoride with very low solubility and 10–30% by weight of the total composition selected from the group consisting of complex heavy-metal fluorides having the general formula $M^{II}M^{IV}F_6$, where $M^{II}$ is selected from the group consisting of calcium, strontium, and barium ions, and $M^{IV}$ is selected from the group consisting of titanium, zirconium, and hafnium ions.

2. A polymerizable radiopaque composition comprising:
   at least one ethylenically unsaturated, polymerizable substance selected from the group consisting of monomers and polymers; and
   a heavy-metal fluoride with very low solubility selected from the group consisting of complex heavy-metal fluorides having the general formula $M^{II}M^{IV}F_6$, where $M^{II}$ is selected from the group consisting of calcium, strontium, and barioum ions, and $M^{IV}$ is selected from the group consisting of titanium, zirconium, and hafnium ions; said heavy-metal fluoride being 5–30% by weight of the total composition.

3. A dental composition according to claim 2, which includes at least one of the group consisting of conventional fillers, pigments, and thixotropic auxiliary material, and also includes at least one polymerization initiator.

4. A polymerizable, radiopaque dental composition comprising:
   at least one ethylenically unsaturated, polymerizable substance selected from the group consisting of monomers and polymers;
   a heavy-metal fluoride with very low solubility selected from the group consisting of complex heavy-metal fluorides having the general formula $M^{II}M^{IV}F_6$, where $M^{II}$ is selected from the group consisting of calcium, strontium, and barium ions, and $M^{IV}$ is selected from the group consisting of titanium, zirconium, and hafnium ions;
   said dental composition including at least one of the group consisting of conventional fillers, pigments, and thixotropic auxiliary material, and also including at least one polymerization initiator; and
   said dental composition further including up to 50% by weight of said monomer and polymer group, 30–70% by weight of said filler, pigment, and thixotropic auxiliary material group, 0.01–5% by weight of said polymerization initiator, and 5–30% by weight of said heavy-metal fluoride group, with all said weight percentages being relative to the total composition.

5. A dental composition according to claim 2, in which said complex heavy-metal fluoride is selected from the group consisting of $SrZrF_6$ and $BaZrF_6$.

6. A dental composition according to claim 2, in which said heavy-metal fluoride has an index of refraction in the range of from 1.45 to 1.60.

7. A dental composition according to claim 2, in which said heavy-metal fluoride is 10–20% by weight of the total composition.

8. A dental composition according to claim 7, in which said heavy-metal fluoride is approximately 15% by weight of the total composition.